United States Patent [19]

Lascombes et al.

[11] Patent Number: 5,326,473
[45] Date of Patent: Jul. 5, 1994

[54] DEVICE FOR EXTEMPORANEOUS AND CONTINOUS PREPARATION OF DIALYSATE

[76] Inventors: Jean-Jacques Lascombes, 21, Rue d'Orleans, 31000 Toulouse; Jean-Michel Pujo, Domaine de Montoussel, Beauville, 31140 Caraman, both of France

[21] Appl. No.: 754,901

[22] Filed: Sep. 4, 1991

[30] Foreign Application Priority Data

Sep. 13, 1990 [FR] France .................. 90 11578

[51] Int. Cl.⁵ ............................................. B01D 24/00
[52] U.S. Cl. ..................... 210/474; 210/321.75; 210/475; 210/295; 220/564; 422/278; 604/406; 604/416
[58] Field of Search ................ 210/475, 647, 321.65, 210/321.84, 295, 321.75, 257.2, 474; 604/416, 605; 366/192, 337; 220/564; 422/278

[56] References Cited

U.S. PATENT DOCUMENTS

| | | | |
|---|---|---|---|
| 3,881,640 | 5/1975 | Noble | 604/406 |
| 4,282,863 | 8/1981 | Beigler et al. | 604/416 |
| 4,346,703 | 8/1982 | Dennehey et al. | 604/406 |
| 4,484,920 | 11/1984 | Kaufman et al. | 604/416 |
| 4,601,704 | 7/1986 | Larkin | 604/416 |
| 4,610,684 | 9/1986 | Knox et al. | 604/416 |
| 4,812,239 | 3/1989 | Mills et al. | 210/647 |
| 4,848,916 | 7/1989 | Mead | 366/192 |
| 4,936,829 | 6/1990 | Zdeb et al. | 604/406 |

FOREIGN PATENT DOCUMENTS

| | | |
|---|---|---|
| 0278100 | 8/1988 | European Pat. Off. . |
| 1410896 | 10/1964 | France . |
| 2604922 | 10/1986 | France . |

*Primary Examiner*—Frank Spear
*Assistant Examiner*—Ana Fortuna
*Attorney, Agent, or Firm*—Auslander & Thomas

[57] ABSTRACT

A container for quick connection and disconnection to a dialysis generator, the container having a substantial amount of solid compound for extemporaneous and continuous preparation of dialysate obtained from dissolution of a concentrate and/or from the solid compound in treated water. A conduit leads the water from an inlet orifice to the container, where the treated water passes through the solid compound and therethrough to and outlet orifice and into the dialysis generator. The water may be directed through a conduit within the container or through a conduit outside the container. The inlet and the outlet orifices may be provided with a micron filter.

9 Claims, 2 Drawing Sheets

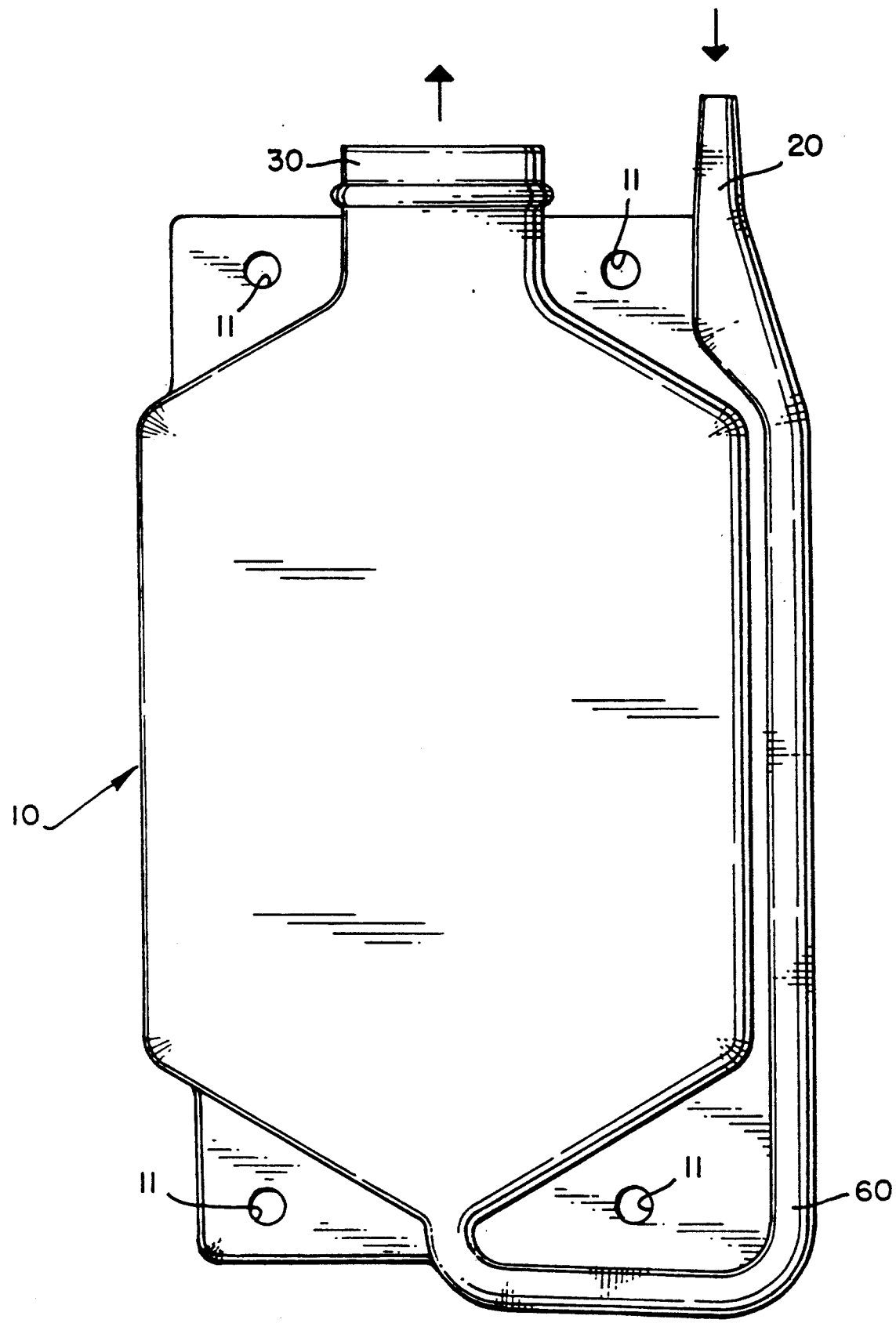

DEVICE FOR EXTEMPORANEOUS AND CONTINOUS PREPARATION OF DIALYSATE

The present invention relates to a device for the extemporaneous and continuous preparation of a dialysis solution by dissolution of a solid compound, in granular or pulverulent form, in purified water.

Such devices are associated with hemodialysis generators which control their operation. Equipments of this kind have been known for some time already. Thus, French Patent Application No. 2,604,922 describes a device which consists schematically of a fixed mixing vat equipped with a water feed pipe and a dialysis liquid outlet line connected to a generator. Into said vat is introduced a defined quantity of compound in solid form delivered from a storage tank by means of a proportioning system, the mixing being ensured by a stirring device.

Besides the complexity of its structure, such a device requires too many manipulations of the compound, which is first taken out of its wrapping to be stored in bulk in a hopper before being poured into the mixing vat.

The device of the invention does not have such disadvantages. In fact, it permits a preliminary conditioning of the solid compound in a tight volume, depending on the predetermined doses required to effect one or more dialysis operations, said volume being then used itself for the preparation of the solution.

More precisely, the invention relates to a device for the extemporaneous and continuous preparation of dialysate, obtained from the dissolution of a concentrated and/or saturated solution prepared by dissolution of a solid compound in water for hemodialysis, said device, which is controlled by a dialysis generator, being remarkable in that it comprises a container for the solid compound, said container being equipped with an inlet orifice for the water for hemodialysis and an outlet orifice for the concentrated and/or saturated solution, to removably connect said container to said generator.

The merit of such a device is readily clear. To perform a dialysis operation it suffices, in fact, to tightly connect a container of the above type to the water outlet and dialysate inlet pipes equipping a generator, which container holds the dose of solid products required for such an operation. After dissolution of the dose of compound in the container and suction of the solution obtained, one disconnects the generator and the used container in order to put in place a new container if desired. The use of such a device results in an obvious saving of time and a great saving of means.

Other characteristics and advantages of the invention will become evident on reading the following description of two examples of realization of a device according to the information given above, these examples being given merely by way of illustration and no restrictive interpretation of the protection sought can be drawn therefrom.

BRIEF DESCRIPTION OF DRAWINGS

This description is accompanied by drawings where:

FIG. 2 represents, in a schematic sectional view, a second form of realization of a container also intended to be connected to a dialysis generator.

DETAILED DESCRIPTION

Figure 1:
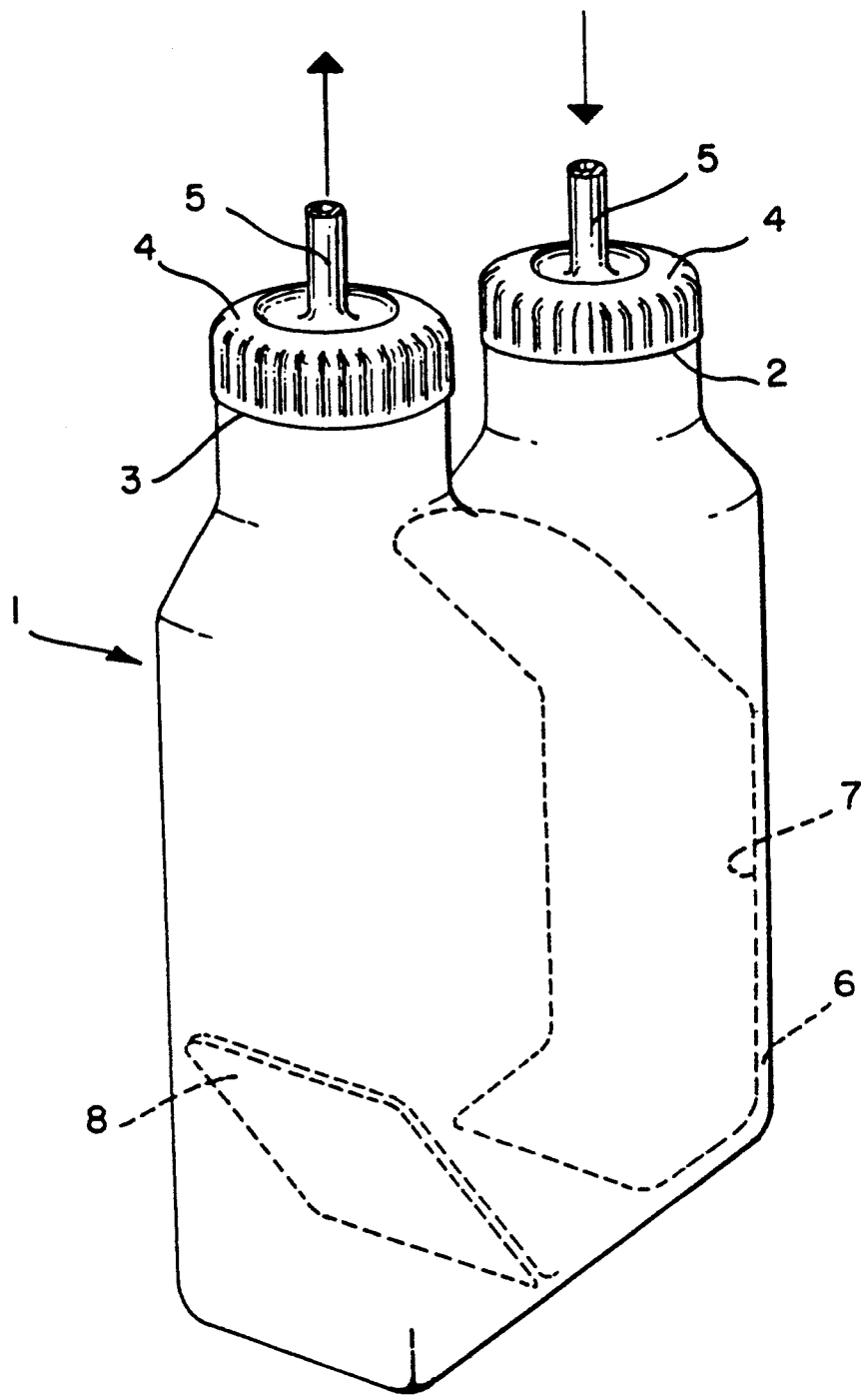
FIG. 1 represents, in a partially sectional perspective view, a first form of realization of a container intended to be connected to a dialysis generator, which it was not found necessary to represent since such an apparatus is well known to the specialists.

The container 1, illustrated in FIG. 1, has the appearance of a bottle of substantially parallelepipedal form, which is equipped with two identical parallel necks. The container comprises in fact two openings situated at the same level in the top part, one, 2, serving as inlet for the purified water, the other, 3, being intended for the outlet of the dialysis liquid obtained after dissolution of the solid compound contained in the container. In the form of realization given as example, the container illustrated is more particularly intended for the conditioning and dissolution of a compound in powder form.

These openings 2 and 3 are closed by tight stoppers 4, equipped with a filter of a porosity between 1 and 100 $\mu$m, each stopper being equipped at its top with a flexible line 5 on which a flow regulating system could be mounted. These flexible lines 5 thus serve as means for connection to the dialysis generator.

To facilitate the diffusion of water into the volume of solid compound, container 1 comprises a conduit 6 intended to channel the flow of water into the bottom part of said container. In the form of realization illustrated, it is a conduit disposed inside the container and is formed by a portion of the wall of the container connecting the upper and lower parts thereof and by an inner partition 7, shown in broken lines, which extends from the edges of the water inlet orifice 2 substantially parallel to said wall portion.

As can be noted further, this conduit 6 discharges in the bottom of the container, substantially in the center of the bottom wall, opposite an inclined portion 8 of said wall. This inclined portion also constitutes a means for obtaining better difficusion of the water in the volume of powder but serves mainly to prevent the accumulation of powder in the respective corner. To this effect, the angle formed between the bottom of container 1 and the inclined wall portion 8 facing the exit of the inner conduit 6 is preferably between 150° and 130°.

Thus, the water entering the container through the orifice 2 is sent by conduit 6 to the bottom of the volume of powder and diffuses through it to become charged with compounds. A concentrated and saturated solution then forms in the top part of the container and is subsequently extracted by suction across the outlet orifice 3.

The container illustrated has a capacity of 2 liters. But it is entirely possible to form containers having the same structural characteristics offering a capacity of 1 to 10 liters and containing 0.5 to 6 kg of solid compound in powder form.

The container 10, illustrated in a sectional view in FIG. 2, also has the appearance of a bottle whose inner walls form between them angles of about 130°, in order to avoid the formation of small heaps of powder in the lower corners of the container.

It is provided with an inlet orifice 20 for the treated water and an outlet orifice 30 for the dialysis solution. As can be seen, the inlet orifice 20 is associated with an outer conduit 60 which discharges substantially in the center of the bottom wall of the container between two inclined portions.

Such a container can be used like that of FIG. 1 in the position as represented, that is, the inlet and outlet orifices 20 and 30 are disposed in the top part of the container. But it can also be used, depending on the type of dialysis generator to which it is connected, in a position inverted by 180°, the inlet and outlet orifices 20 and 30 being then disposed in the bottom part and the treated water being thus conveyed by conduit 60 to the top of the volume of powder. This latter position offers notably the advantage of avoiding the formation of air bubbles at the level of the outlet of the dialysis solution.

To permit the use of the container in one or the other position indiscriminately, the latter is provided with suspension lugs 11 located at its four corners.

The containers illustrated in FIGS. 1 and 2 will preferably be obtained by molding of a plastic material whose physical-chemical qualities will be appropriate for the particular use of said containers.

We claim:

1. Device for the extemporaneous and continuous preparation of a dialysate for use in a dialysis generator, said dialysate obtained from the dissolution of a concentrate and/or saturated solution prepared by dissolving a solid compound in treated water, said device comprising a container having a solid compound therein and having atop and bottom surfaces, said container being provided with means defining and inlet orifice for said treated water and means defining an outlet orifice for said dialysis solution, said inlet orifice having means for removable connecting a water outlet pipe in said dialysis generator, and said outlet orifice having means for removable connecting a dialysate inlet pipe in said dialysis generator, said inlet orifice for said treated water having a conduit leading said treated water to said solid compound in said container, and said conduit inside said container, said conduit formed by a portion of a wall of the container connecting the top and bottom surfaces thereof and by an inner partition thereof extending from said inlet orifice substantially parallel to said wall portion to an area near said bottom surface.

2. Device according to claim 1, wherein said inlet orifice for said treated water and outlet orifice for said dialysis solution are provided with a filter of a porosity between 1 and 100.

3. The invention of claim 7 wherein said inlet orifice for said treated water and said outlet orifice for said dialysis solution are situated at the same surface of said container.

4. The invention of claim 1, wherein said conduit leading water to said solid compound opens at the bottom surface of said container.

5. Device for use with a dialysis generator including a water inlet pipe and a water outlet pipe, and for extemporaneous and continuous preparation of dialysate obtained for the dissolution of a concentrated and or saturated solution, prepared by dissolving a solid in treated water, said device comprising a container having top and bottom surfaces and a solid compound therein, said container being provided with means positioned on said top surface for defining an inlet orifice, means positioned on an communicating through said top surface for defining an outlet orifice for removing a dialysate solution from the container, said inlet orifice being connected to a conduit extending outside the container and leading treated water to the container through an inlet positioned and communicating through said bottom surface of said container, means for removable connecting said inlet orifice to said water outlet of said dialysis generator, and means for removable connecting said outlet orifice to said inlet pipe of said dialysis generator.

6. Device according to claim 5, wherein said container includes means to avoid accumulation of said solid compound.

7. Device according to claim 6, wherein said means to avoid accumulation of said solid compound comprise at least one inclined portion of the inner wall of the container.

8. Device according to claim 7, wherein said means to avoid accumulation of said solid compound includes an inclined portion having an angle between 150° and 130° with the inner wall of the container.

9. Device for use with a dialysis generator, for extemporaneous and continuous preparation of dialysate, obtained from the dissolution of a concentrate and/or saturated solution prepared by dissolving a solid compound in treated water, said device comprising a container having said solid compound therein, said container being provided with means defining and inlet orifice for said treated water, and with means defining an outlet orifice for removing said dialysis solution, said inlet orifice having means for removable connecting a water pipe of a dialysis generator, and said outlet orifice having means for removable connecting a dialysate inlet pipe of said dialysis generator, said inlet orifice for said treated water having a conduit leading said treated water to said solid compound in said container, and said container having a capacity of 1 to 10 liters and contains 0.5 to 6 Kg of solid compound in powder form.

* * * * *

UNITED STATES PATENT AND TRADEMARK OFFICE
CERTIFICATE OF CORRECTION

PATENT NO. : 5,326,473
DATED : July 5, 1994
INVENTOR(S) : Jean-Jacques Lascombes, et al It is certified that error appears in the above-identified patent and that said Letters Patent is hereby corrected as shown below:

IN THE CLAIMS

Column 3:
Claim 1, line 7, after "having", insert and change "atop" to -- a top -- line 8, insert and change "and" to -- an --

Claim 2, line 4, after "100", insert -- $\mu$ --

Claim 3, line 1, insert and change "7" to -- 1 --

Column 4:
Claim 9, line 7, insert and change "and" to -- an --

Signed and Sealed this

Fourth Day of April, 1995

BRUCE LEHMAN

*Attest:*

*Attesting Officer*        Commissioner of Patents and Trademarks